US010441638B2

(12) United States Patent
Greenfield et al.

(10) Patent No.: US 10,441,638 B2
(45) Date of Patent: Oct. 15, 2019

(54) CYCLIC ACETYLCHOLINESTERASE C-TERMINAL PEPTIDE IN THE TREATMENT OR PREVENTION OF CANCER OR METASTASIS

(71) Applicant: NEURO-BIO LTD, Abingdon, Oxfordshire (GB)

(72) Inventors: Susan Adele Greenfield, Abingdon (GB); Christopher Pepper, Cardiff (GB)

(73) Assignee: Neuro-Bio Ltd., Abingdon (GB)

( * ) Notice: Subject to any disclaimer, the term of this patent is extended or adjusted under 35 U.S.C. 154(b) by 0 days.

(21) Appl. No.: 15/535,020

(22) PCT Filed: Dec. 18, 2015

(86) PCT No.: PCT/GB2015/054068
§ 371 (c)(1),
(2) Date: Jun. 9, 2017

(87) PCT Pub. No.: WO2016/097753
PCT Pub. Date: Jun. 23, 2016

(65) Prior Publication Data
US 2017/0368151 A1    Dec. 28, 2017

(30) Foreign Application Priority Data

Dec. 19, 2014 (GB) .................................. 1422715.1
May 18, 2015 (GB) .................................. 1508480.9

(51) Int. Cl.
| A61K 38/12 | (2006.01) |
| A61P 35/00 | (2006.01) |
| A61K 38/00 | (2006.01) |
| A61P 35/02 | (2006.01) |
| A61K 38/10 | (2006.01) |
| A61P 35/04 | (2006.01) |
| C07K 5/00 | (2006.01) |
| C07K 7/00 | (2006.01) |
| C07K 16/00 | (2006.01) |
| C07K 17/00 | (2006.01) |
| A61K 38/04 | (2006.01) |
| A61K 38/46 | (2006.01) |
| C12N 9/18 | (2006.01) |

(52) U.S. Cl.
CPC ............ *A61K 38/465* (2013.01); *A61K 38/12* (2013.01); *A61P 35/02* (2018.01); *A61P 35/04* (2018.01); *C12N 9/18* (2013.01); *C12Y 301/01007* (2013.01); *A61K 38/00* (2013.01)

(58) Field of Classification Search
None
See application file for complete search history.

(56) References Cited

U.S. PATENT DOCUMENTS

| 10,053,677 | B2 * | 8/2018 | Greenfield | ............... C07K 7/64 |
| 2004/0204348 | A1 | 10/2004 | Jones et al. | |
| 2009/0169520 | A1 | 7/2009 | Soreq et al. | |

FOREIGN PATENT DOCUMENTS

| EP | 2 754 451 A1 | 7/2014 | |
| WO | WO 97/35962 A1 | 10/1997 | |
| WO | WO-9735962 A1 * | 10/1997 | ............. C07K 16/40 |
| WO | WO 98/02452 A2 | 1/1998 | |
| WO | WO 00/73427 A2 | 12/2000 | |
| WO | WO-0073427 A2 * | 12/2000 | ............. C07K 16/40 |
| WO | WO 2007/049281 A1 | 5/2007 | |

OTHER PUBLICATIONS

Onganer et al "An acetylcholinesterase-derived peptide inhibits endocytic membrane activity in a human metastatic breast cancer cell line" Biochemica et Biophysica Acta 1760:415-420. (Year: 2006).*
Goodwin et al. "Peptides as Therapeutics with Enhanced Bioactivity" Current Medicinal Chemistry 19:4451-4461. (Year: 2012).*
International Search report and written opinion dated Mar. 15, 2016 in PCT/GB2015/054068 filed Dec. 18, 2015, 15 pages.
International Preliminary Report on Patentability dated Feb. 23, 2017 in PCT/GB2015/054068 filed Dec. 18, 2015, 17 pages.
Onganer et al., "An acetylcholinesterase-derived peptide inhibits endocytic membrane activity in a human metastatic breast cancer cell line", Biochimica Et Biophysica Acta (Bba) General Subjects, Elsevier, Amsterdam, NL, vol. 1760, No. 3, Mar. 1, 2006, pp. 415-420, XP025014834.

* cited by examiner

*Primary Examiner* — Christina Bradley
*Assistant Examiner* — Zachary J Miknis
(74) *Attorney, Agent, or Firm* — Squire Patton Boggs (US) LLP

(57) ABSTRACT

The invention relates to cyclic polypeptides derived from the C-terminus of acetylcholinesterase for use in treating or preventing cancer or metastatic disease.

3 Claims, 13 Drawing Sheets

Specification includes a Sequence Listing.

CYCLIC ACETYLCHOLINESTERASE C-TERMINAL PEPTIDE IN THE TREATMENT OR PREVENTION OF CANCER OR METASTASIS

CROSS-REFERENCE TO RELATED APPLICATIONS

This application is a national stage of international application no. PCT/GB2015/054068, filed Dec. 18, 2015, which claims benefit of Great Britain application no. 1508480.9, filed May 18, 2015, and of Great Britain application no. 1422715.1, filed Dec. 19, 2014, the contents of each of which are hereby incorporated by reference in their entireties.

The invention relates to cancers, and in particular to novel compositions, therapies and methods for treating, preventing or ameliorating cancer or metastatic disease.

Cancer and malignant tumours form a group of diseases involving abnormal cell growth with the potential to invade or spread to other parts of the body, i.e. metastasis. In 2012, approximately 14 million new cases of cancer occurred globally. There is therefore a need to provide an improved medicament for the treatment of cancer, and metastasis.

The inventors investigated the effects of a cyclic peptide derived from the C-terminus of acetylcholinesterase (known as "NBP-14") on various cancer cell lines, as well as primary tumour cells derived from patients and lymphocytes derived from healthy age-matched individuals, and found that it showed modest apoptotic and anti-proliferative activity in each of the cancer cell lines tested. In addition, they have also shown that the cyclic peptide is non-toxic in normal cells. Accordingly, the inventors believe that cyclic peptides will have therapeutic benefit in the treatment of cancer, tumours and metastatic disease.

Thus, in a first aspect of the invention, there is provided a cyclic polypeptide, derivative or analogue thereof, for use in treating, ameliorating or preventing cancer or metastatic disease.

In a second aspect, there is provided a method of treating, ameliorating or preventing cancer or metastatic disease in a subject, the method comprising, administering to a subject in need of such treatment, a therapeutically effective amount of a cyclic polypeptide, derivative or analogue thereof.

As described in the Examples, the inventors performed in vitro cytotoxicity testing of a cyclic peptide derived from the C-terminus of acetylcholinesterase (known as "NBP-14") on: (i) primary chronic lymphocytic leukaemia (CLL) samples derived from CLL patients with a range of prognostic markers (MEC-1 cells); (ii) in KG1a (Acute myeloid leukaemia cell line) and H929 and JJN3 (Multiple myeloma cell lines); and (iii) in MCF7 and MDA-MB-231 (breast cancer cell lines). The inventors have surprisingly shown that the cyclic peptide, NBP-14, showed apoptotic effects in each of the cell lines tested at concentrations>0.1 µM. Moreover, MCF7 cells showed increased sensitivity to NBP-14. The cyclic peptide, NBP-14, showed evidence of anti-proliferative activity in MDA-MB-231 cells, and similar effects were also observed in JJN3 cells, KG1a cells, MEC-1 cells and H929 cells with concentrations of peptide>0.1 µM. Advantageously, they have also shown that the cyclic peptide is non-toxic in normal cells at the same concentrations.

The cancer which is treated may be leukaemia. For example, the cancer may be lymphocytic leukaemia or chronic lymphocytic leukaemia (CLL). The cancer may be myeloid leukaemia, or acute myeloid leukaemia. The cancer may be multiple myeloma. The cancer may be breast cancer.

Most preferably, the cyclic polypeptide, derivative or analogue thereof, is for use in treating, ameliorating or preventing metastatic disease.

Cyclic polypeptides are peptide chains whose N- and C-termini are themselves linked together with a peptide bond that forms a circular chain of amino acids, as shown in FIG. 8B.

The term "derivative or analogue thereof" can mean a polypeptide within which amino acid residues are replaced by residues (whether natural amino acids, non-natural amino acids or amino acid mimics) with similar side chains or peptide backbone properties. Additionally, the terminals of such peptides may be protected by N- and C-terminal protecting groups with similar properties to acetyl or amide groups.

Derivatives and analogues of peptides according to the invention may also include those that increase the peptide's half-life in vivo. For example, a derivative or analogue of the peptides of the invention may include peptoid and retropeptoid derivatives of the peptides, peptide-peptoid hybrids and D-amino acid derivatives of the peptides.

Peptoids, or poly-N-substituted glycines, are a class of peptidomimetics whose side chains are appended to the nitrogen atom of the peptide backbone, rather than to the alpha-carbons, as they are in amino acids. Peptoid derivatives of the peptides of the invention may be readily designed from knowledge of the structure of the peptide. Retropeptoids (in which all amino acids are replaced by peptoid residues in reversed order) are also suitable derivatives in accordance with the invention. A retropeptoid is expected to bind in the opposite direction in the ligand-binding groove, as compared to a peptide or peptoid-peptide hybrid containing one peptoid residue. As a result, the side chains of the peptoid residues are able point in the same direction as the side chains in the original peptide.

Preferably, the cyclic polypeptide, derivative or analogue thereof comprises or consists of an amino acid sequence derived from the C-terminus of acetylcholinesterase (AChE), or a truncation thereof.

As described in the Examples, the inventors were very surprised to observe that the cyclic AChE-derived polypeptides of the invention selectively target tumour cells rather than normal tissue.

Hence, the term "derived from" can mean an amino acid sequence, which is a derivative or a modification of an amino acid sequence that is present in, or forms, the C-terminus of AChE, and portion thereof.

The term "truncation thereof" can mean the cyclic polypeptide derived from AChE is reduced in size by the removal of amino acids. The reduction of amino acids may be achieved by removal of residues from the C- or N-terminal of the peptide prior to cyclisation into the cyclic polypeptide of the invention, or may be achieved by deletion of one or more amino acids from within the core of the peptide prior to cyclisation.

Acetylcholinesterase is a serine protease that hydrolyses acetylcholine, and will be well-known to the skilled person. The major form of acetylcholinesterase which is found in the brain is known as tailed acetylcholinesterase (T-AChE). It is especially preferred that the cyclic polypeptide, derivative or analogue thereof comprises an amino acid sequence derived from the C-terminus of tailed acetylcholinesterase (T-AChE), or a truncation thereof.

The protein sequence of one embodiment of human tailed acetylcholinesterase (Gen Bank: AAA68151.1) is 614 amino acids in length, and is provided herein as SEQ ID No:1, as follows:

```
                                                                           [SEQ ID No: 1]
  1 mrppqcllht pslaspllll llwllgggvg aegredaell vtvrggrlrg irlktpggpv 61 saflgipfae ppmgprrflp pepkqpwsgv vdattfqsvc yqyvdtlypg fegtemwnpn 121 relsedclyl nvwtpyprpt sptpvlvwiy gggfysgass ldvydgrflv qaertvlvsm 181 nyrvgafgfl alpgsreapg nvglldqrla lqwvqenvaa fggdptsvtl fgesagaasv 241 gmhllsppsr glfhravlqs gapngpwatv gmgearrrat qlahlvgcpp ggtggndtel 301 vaclrtrpaq vlvnhewhvl pqesvfrfsf vpvvdgdfls dtpealinag dfhglqvlvg 361 vvkdegsyfl vygapgfskd neslisraef lagvrvgvpq vsdlaaeavv lhytdwlhpe 421 dparlreals dvvgdhnvvc pvaqlagrla aqgarvyayv fehrastlsw plwmgvphgy 481 eiefifgipl dpsrnytaee kifaqrlmry wanfartgdp neprdpkapq wppytagaqq 541 yvsldlrple vrrglraqac afwnrflpkl lsatdtldea erqwkaefhr wssymvhwkn 601 qfdhyskqdr csdl
```

It will be appreciated that the first 31 amino acid residues of SEQ ID No:1 are removed while the protein is released, thereby leaving a 583 amino acid sequence. Accordingly, it is preferred that the cyclic polypeptide, derivative or analogue thereof comprises or consists of an amino acid sequence derived from the C-terminus of acetylcholinesterase, or a truncation thereof, wherein the acetylcholinesterase comprises an amino acid sequence substantially as set out in SEQ ID No:1, preferably excluding the 31 amino acids at the N-terminal.

Preferably, the cyclic polypeptide, derivative or analogue thereof comprises or consists of an amino acid sequence derived from the last 300, 200, 100 or 50 amino acids forming the C-terminus of acetylcholinesterase, or a truncation thereof, most preferably wherein the acetylcholinesterase comprises or consists of an amino acid sequence substantially as set out in SEQ ID No:1. The cyclic polypeptide, derivative or analogue thereof preferably comprises or consists of an amino acid sequence derived from the last 40 amino acids forming the C-terminus of acetylcholinesterase, or a truncation thereof.

Preferably, the cyclic polypeptide, derivative or analogue thereof comprises or consists of between 8 and 40 amino acid residues, more preferably between 10 and 30 amino acids, and most preferably between 12 and 20 amino acids. The inventor has prepared three peptide sequences that are derived from the C-terminus of AChE, and which are referred to herein as T30, T14 and T15, where the number corresponds to the amino acid number.

The amino acid sequence of T30 (which corresponds to the last 30 amino acid residues of SEQ ID No:1) is provided herein as SEQ ID No:2, as follows:

[SEQ ID No: 2]
KAEFHRWSSYMVHWKNQFDHYSKQDRCSDL

The amino acid sequence of T14 (which corresponds to the 14 amino acid residues located towards the end of SEQ ID No:1, and lacks the final 15 amino acids found in T30) is provided herein as SEQ ID No:3, as follows:

[SEQ ID No: 3]
AEFHRWSSYMVHWK

The amino acid sequence of T15 (which corresponds to the last 15 amino acid residues of SEQ ID No:1) is provided herein as SEQ ID No:4, as follows:

[SEQ ID No: 4]
NQFDHYSKQDRCSDL

It will be appreciated that any of the sequences represented as SEQ ID No:2-4 can be readily cyclised or cyclated to form a cyclic polypeptide of the first aspect. For example, cyclization of peptides can be achieved by side-chain-to-side-chain, side-chain-to-backbone, or head-to-tail (C-terminus to N-terminus) cyclization techniques. In one preferred embodiment, head-to-tail cyclization is the preferred method by which the cyclic polypeptides are produced. The cyclic polypeptides may be synthesised using either classical solution-phase linear peptide cyclization or resin-based cyclization. Preferred methods for cyclization are described in the Examples. In another preferred embodiment, the polypeptide is produced using a cyclization cleavage approach, in which the cyclic polypeptide is synthesized by cyclization after step-wise linear peptide synthesis. An advantage of this method is that the side-chain does not need to be anchored, making the approach more general. Preferably, prior to use, resultant samples of cyclic peptides can be analysed by MALDI-TOF MS.

Accordingly, a preferred polypeptide according to the invention comprises or consists of cyclic SEQ ID No:2, 3 or 4, or a functional variant or fragment thereof.

The inventors found that cyclated SEQ ID No: 3 (i.e. referred to herein as "cyclated T14", "CT14" or "NBP-14") surprisingly showed selective apoptotic and anti-proliferative activity in each of the cancer cell lines tested compared to healthy cells, and was non-toxic in the normal, non-cancerous cells.

Accordingly, a most preferred cyclic polypeptide of the first aspect comprises or consists of cyclic SEQ ID No:3, or a functional variant or fragment thereof.

It will be appreciated that the cyclic polypeptide according to the invention may be used in a medicament, which may be used as a monotherapy (i.e. use of the cyclic polypeptide, derivative or analogue thereof alone), for treating, ameliorating, or preventing cancer or metastasis. Alternatively, the cyclic polypeptide according to the invention may be used as an adjunct to, or in combination with, known therapies for treating, ameliorating, or preventing cancer.

The cyclic polypeptide according to the invention may be combined in compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well-tolerated by the subject to whom it is given, and preferably enables delivery of the cyclic polypeptide across the blood-brain barrier when treating brain tumours.

Cyclic polypeptides according to the invention may also be incorporated within a slow- or delayed-release device. Such devices may, for example, be inserted on or under the skin, and the medicament may be released over weeks or even months. The device may be located at least adjacent the treatment site. Such devices may be particularly advantageous when long-term treatment with cyclic polypeptides used according to the invention is required and which would normally require frequent administration (e.g. at least daily injection).

In a preferred embodiment, medicaments according to the invention may be administered to a subject by injection into the blood stream or directly into a site requiring treatment. For example, the medicament may be injected at least adjacent the brain. Injections may be intravenous (bolus or infusion) or subcutaneous (bolus or infusion), or intradermal (bolus or infusion).

It will be appreciated that the amount of the cyclic polypeptide that is required is determined by its biological activity and bioavailability, which in turn depends on the mode of administration, the physiochemical properties of the cyclic polypeptide and whether it is being used as a monotherapy or in a combined therapy. The frequency of administration will also be influenced by the half-life of the cyclic polypeptide within the subject being treated. Optimal dosages to be administered may be determined by those skilled in the art, and will vary with the particular cyclic polypeptide in use, the strength of the pharmaceutical composition, the mode of administration, and the advancement of the cancer or metastasis. Additional factors depending on the particular subject being treated will result in a need to adjust dosages, including subject age, weight, gender, diet, and time of administration.

Generally, a daily dose of between 0.001 µg/kg of body weight and 10 mg/kg of body weight, or between 0.01 µg/kg of body weight and 1 mg/kg of body weight, of the cyclic polypeptide according to the invention may be used for treating, ameliorating, or preventing cancer or metastasis, depending upon which cyclic polypeptide is used.

The cyclic polypeptide may be administered before, during or after onset of cancer. Daily doses may be given as a single administration (e.g. a single daily injection or inhalation of a nasal spray). Alternatively, the cyclic polypeptide may require administration twice or more times during a day. As an example, cyclic polypeptides may be administered as two (or more depending upon the severity of the cancer or metastasis being treated) daily doses of between 0.07 µg and 700 mg (i.e. assuming a body weight of 70 kg). A patient receiving treatment may take a first dose upon waking and then a second dose in the evening (if on a two dose regime) or at 3- or 4-hourly intervals thereafter. Alternatively, a slow release device may be used to provide optimal doses of cyclic polypeptide according to the invention to a patient without the need to administer repeated doses.

Known procedures, such as those conventionally employed by the pharmaceutical industry (e.g. in vivo experimentation, clinical trials, etc.), may be used to form specific formulations of the cyclic polypeptide according to the invention and precise therapeutic regimes (such as daily doses of the agents and the frequency of administration). The inventors believe that they are the first to suggest an anti-cancer treatment composition, based on the use of a cyclic polypeptide of the invention.

Hence, in a third aspect of the invention, there is provided an anti-cancer or anti-metastatic pharmaceutical composition comprising a therapeutically effective amount of the cyclic polypeptide, derivative or analogue thereof according to the first aspect, and optionally a pharmaceutically acceptable vehicle.

The invention also provides in a fourth aspect, a process for making the anti-cancer or anti-metastatic pharmaceutical composition according to the third aspect, the process comprising combining a therapeutically effective amount of the cyclic polypeptide, derivative or analogue thereof according to the first aspect, with a pharmaceutically acceptable vehicle.

The cyclic polypeptide, derivative or analogue thereof preferably comprises or consists of Cyclic T14 (i.e. NBP-14) as disclosed herein, i.e. SEQ ID No:3.

A "subject" may be a vertebrate, mammal, or domestic animal. Hence, medicaments according to the invention may be used to treat any mammal, for example livestock (e.g. a horse), pets, or may be used in other veterinary applications. Most preferably, however, the subject is a human being.

A "therapeutically effective amount" of cyclic polypeptide is any amount which, when administered to a subject, is the amount of active agent that is needed to treat the cancer or metastasis, or produce the desired effect. The cyclic polypeptide, derivative or analogue thereof may be used as an adjuvant for the treatment of solid or metastatic tumours, for example with chemotherapy or radiotherapy. This means that lower doses and exposure times of chemotherapy and/or radiotherapy are required.

For example, the therapeutically effective amount of cyclic polypeptide used may be from about 0.001 mg to about 800 mg, and preferably from about 0.01 mg to about 500 mg.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. However, the pharmaceutical vehicle may be a liquid, and the pharmaceutical composition is in the form of a solution. Liquid pharmaceutical compositions, which are sterile solutions or suspensions, can be utilized by, for example, intramuscular, intrathecal, epidural, intraperitoneal, intravenous and particularly subcutaneous injection.

The cyclic polypeptide and compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The cyclic polypeptide used according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

It will be appreciated that the invention extends to any nucleic acid or peptide or variant, derivative or analogue thereof, which comprises substantially the amino acid or nucleic acid sequences of any of the sequences referred to herein, including functional variants or functional fragments thereof. The terms "substantially the amino acid/nucleotide/peptide sequence", "functional variant" and "functional fragment", can be a sequence that has at least 40% sequence identity with the amino acid/nucleotide/peptide sequences of any one of the sequences referred to herein, for example 40% identity with the sequence identified as SEQ ID No:1-4, and so on.

Amino acid/polynucleotide/polypeptide sequences with a sequence identity which is greater than 65%, more preferably greater than 70%, even more preferably greater than 75%, and still more preferably greater than 80% sequence identity to any of the sequences referred to are also envisaged. Preferably, the amino acid/polynucleotide/polypeptide sequence has at least 85% identity with any of the sequences referred to, more preferably at least 90% identity, even more preferably at least 92% identity, even more preferably at least 95% identity, even more preferably at least 97% identity, even more preferably at least 98% identity and, most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on: (i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: END-GAP=−1, and GAPDIST=4. Those skilled in the art will be aware that it may be necessary to vary these and other parameters for optimal sequence alignment.

Preferably, calculation of percentage identities between two amino acid/polynucleotide/polypeptide sequences may then be calculated from such an alignment as (N/T)*100, where N is the number of positions at which the sequences share an identical residue, and T is the total number of positions compared including gaps but excluding overhangs. Hence, a most preferred method for calculating percentage identity between two sequences comprises (i) preparing a sequence alignment using the ClustalW program using a suitable set of parameters, for example, as set out above; and (ii) inserting the values of N and T into the following formula:

Sequence Identity=$(N/T)*100$.

Alternative methods for identifying similar sequences will be known to those skilled in the art. For example, a substantially similar nucleotide sequence will be encoded by a sequence, which hybridizes to DNA sequences or their complements under stringent conditions. By stringent conditions, we mean the nucleotide hybridises to filter-bound DNA or RNA in 3× sodium chloride/sodium citrate (SSC) at approximately 45° C. followed by at least one wash in 0.2×SSC/0.1% SDS at approximately 20-65° C. Alternatively, a substantially similar polypeptide may differ by at least 1, but less than 5, 10, 20, 50 or 100 amino acids from the sequences shown in SEQ ID No: 1-4.

Due to the degeneracy of the genetic code, it is clear that any nucleic acid sequence described herein could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which:

FIG. 1 is a comparison of the cytotoxic effects of T15 (SEQ ID No:4), T30 (SEQ ID No:2), and one embodiment of a cyclic polypeptide according to the invention, i.e.

NBP-14 (SEQ ID No:3), in the breast cancer cell lines (A) MCF7 and (B) MDA-MB-231. All assays were carried out in duplicate and are presented as mean (±SD) of three independent experiments;

Figure 4A:
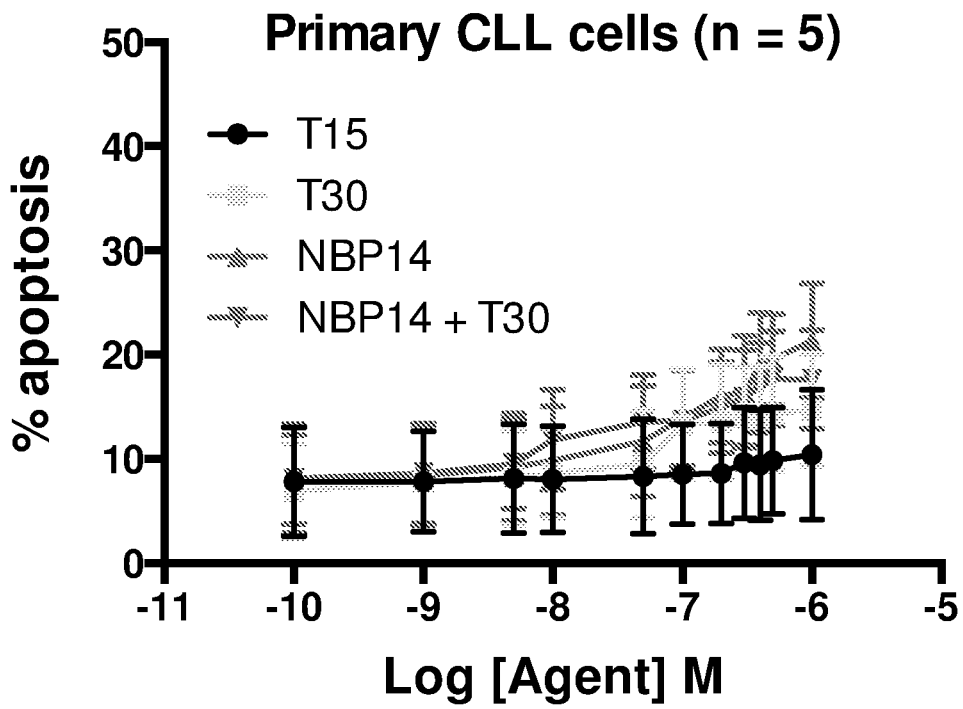
Figure 4B:
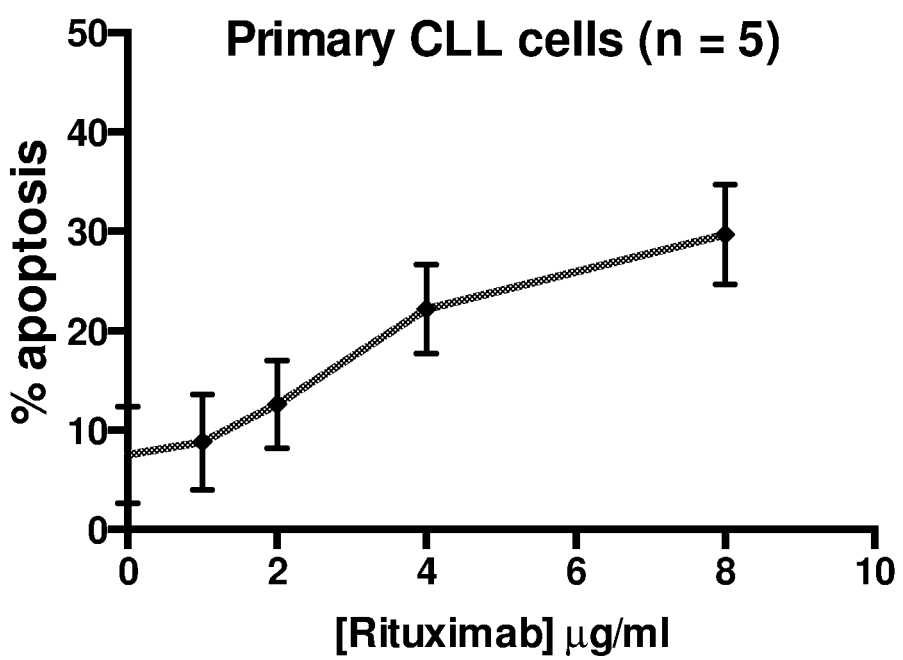
Figure 5:
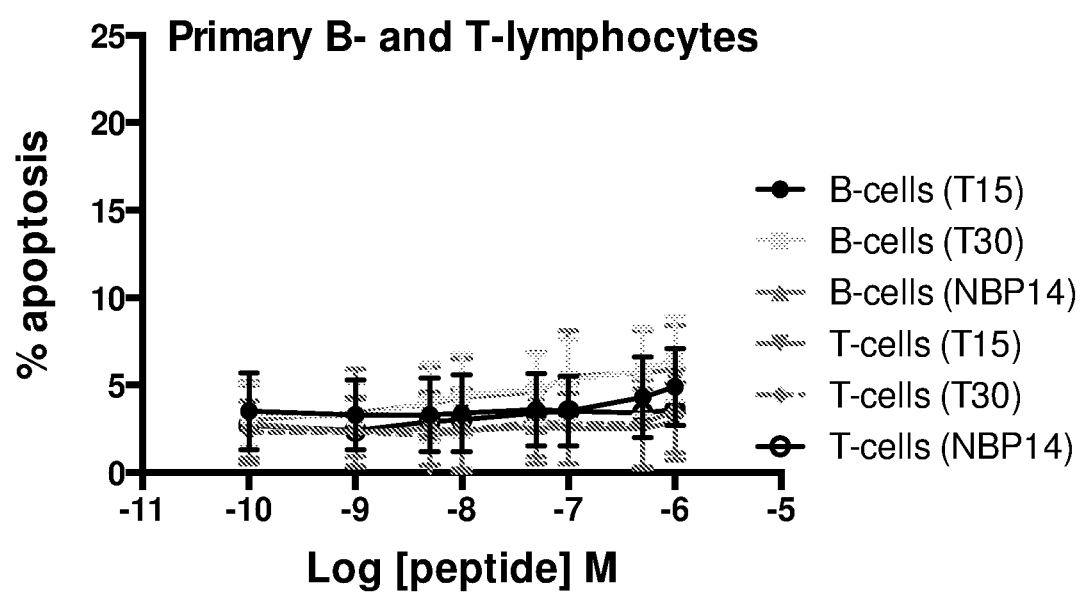
Figure 8A:
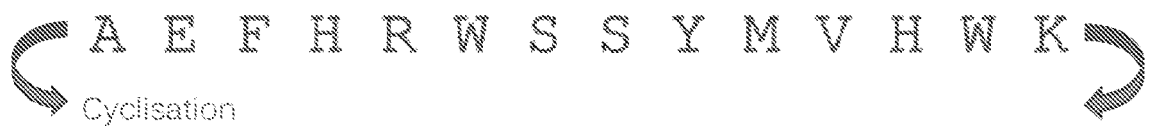
Figure 8B:
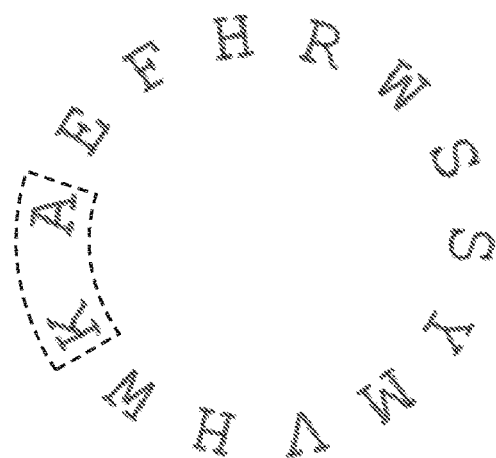
Figure 9:
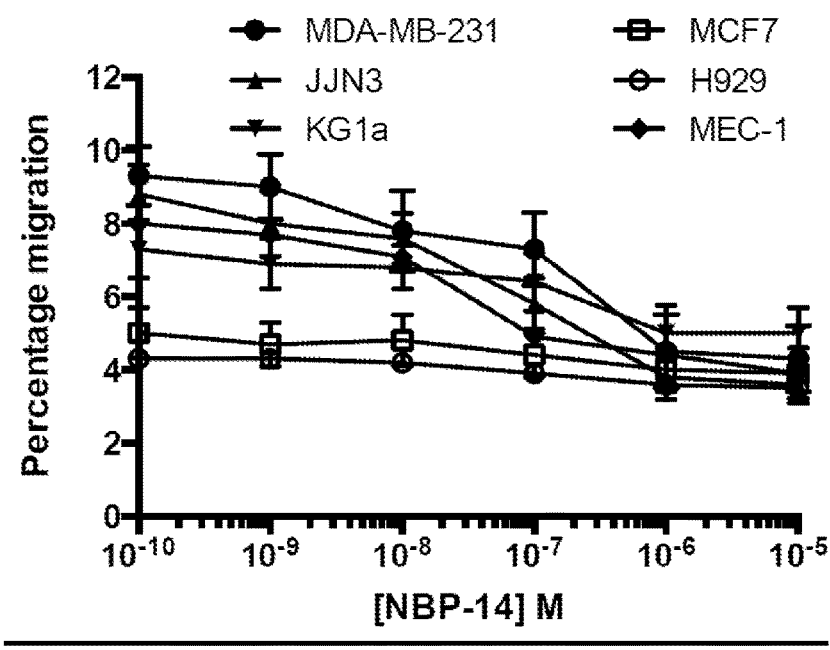
Figure 10A:
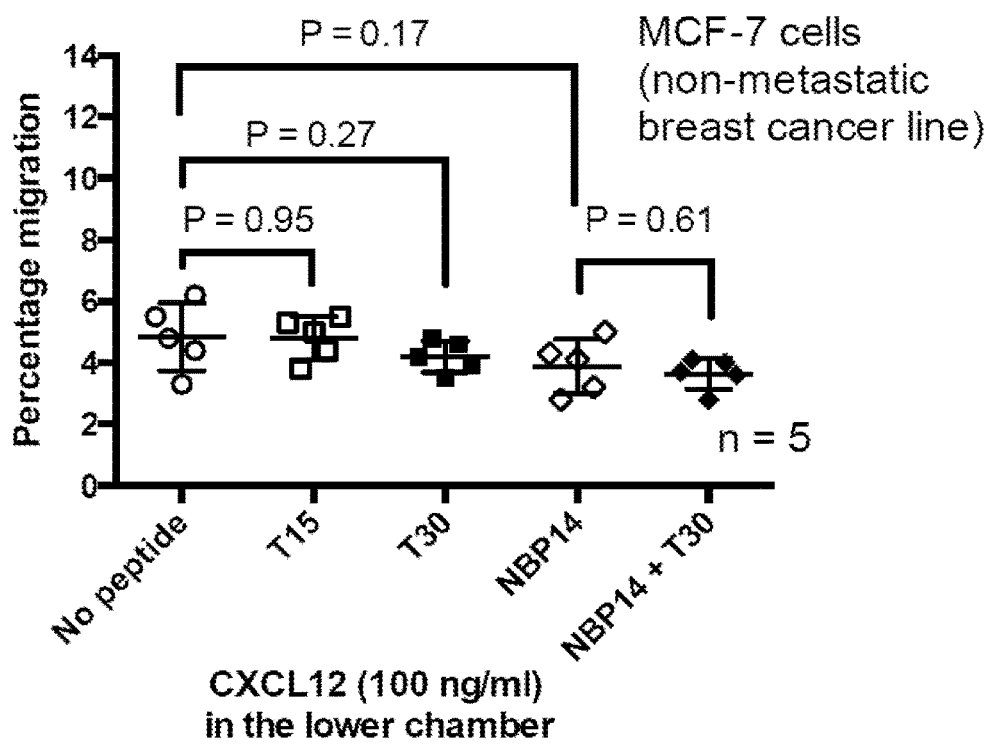
Figure 10B:
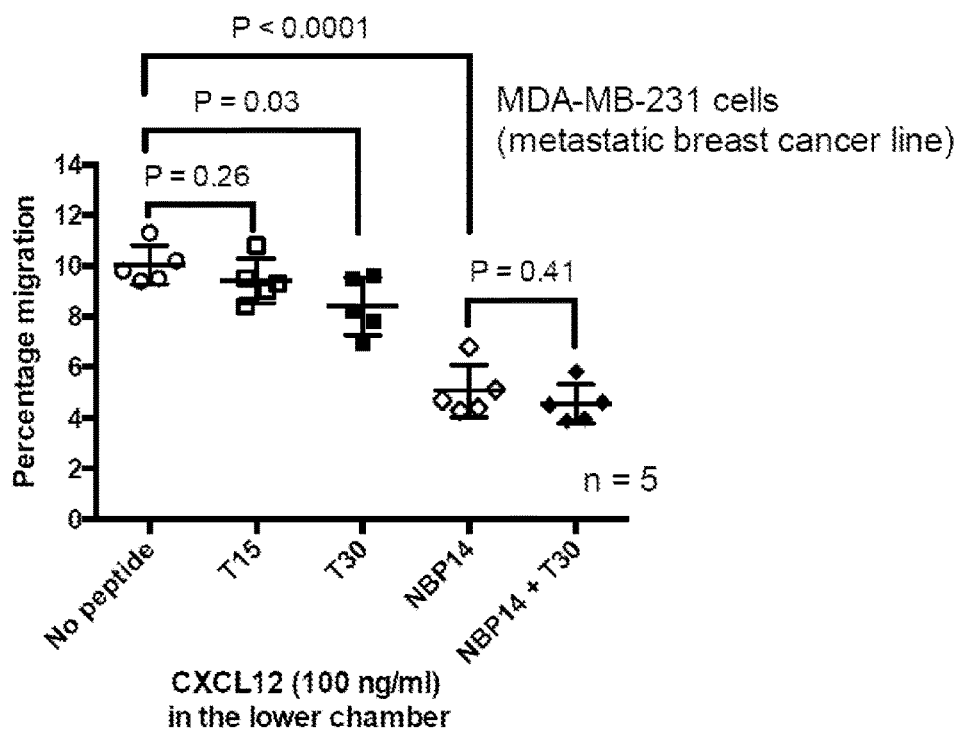
Figure 11:
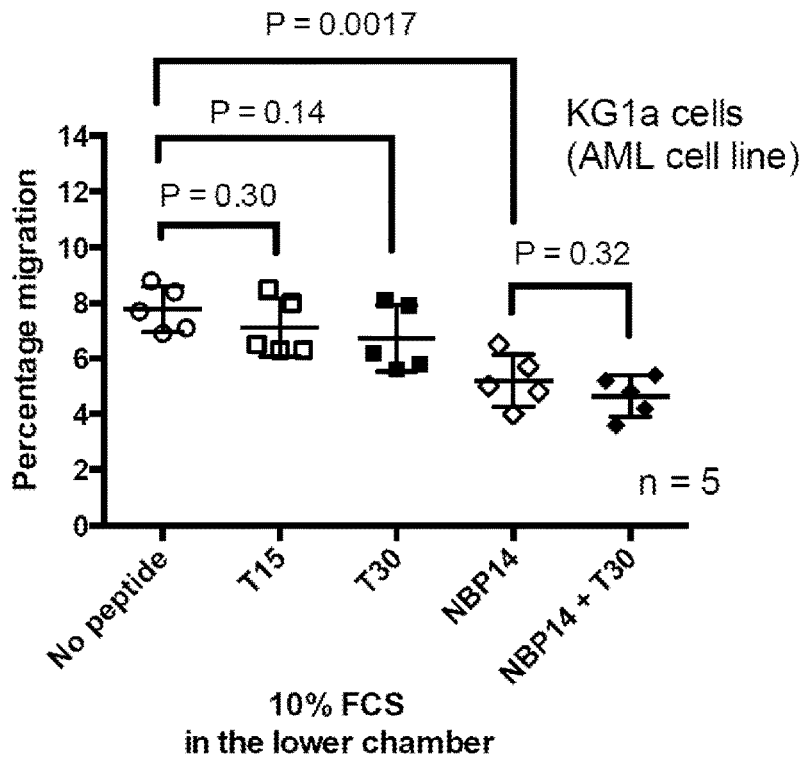
Figure 12:
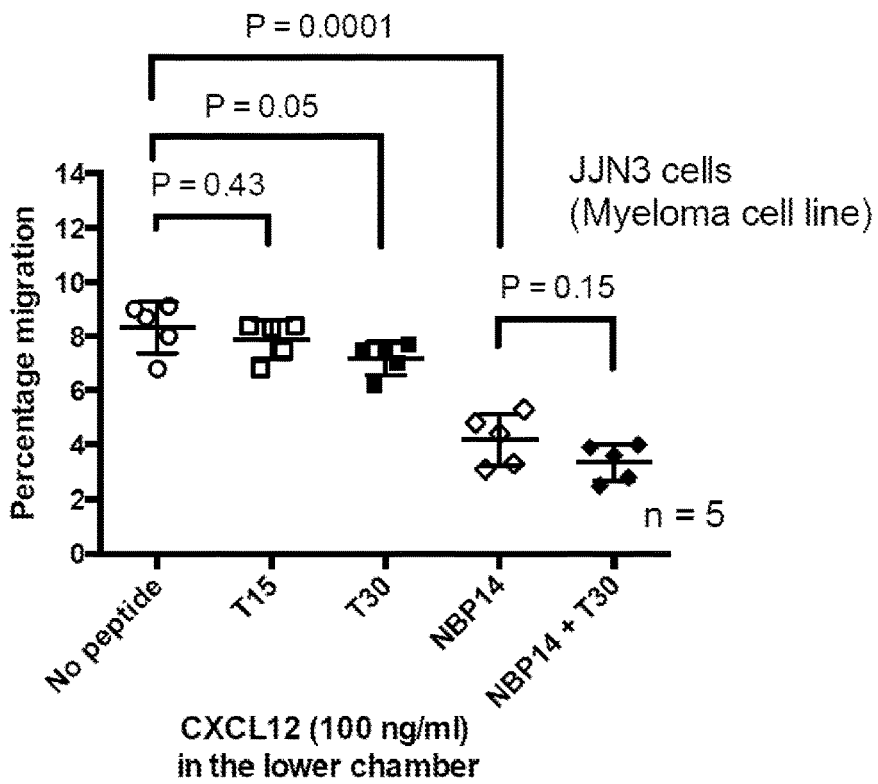
Figure 13:
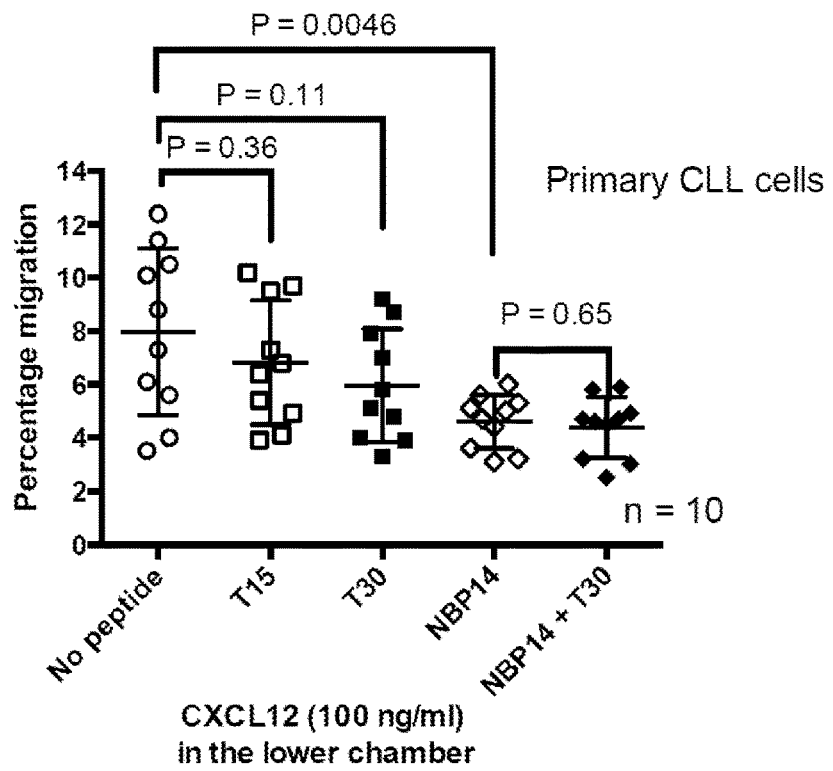
Figure 14:
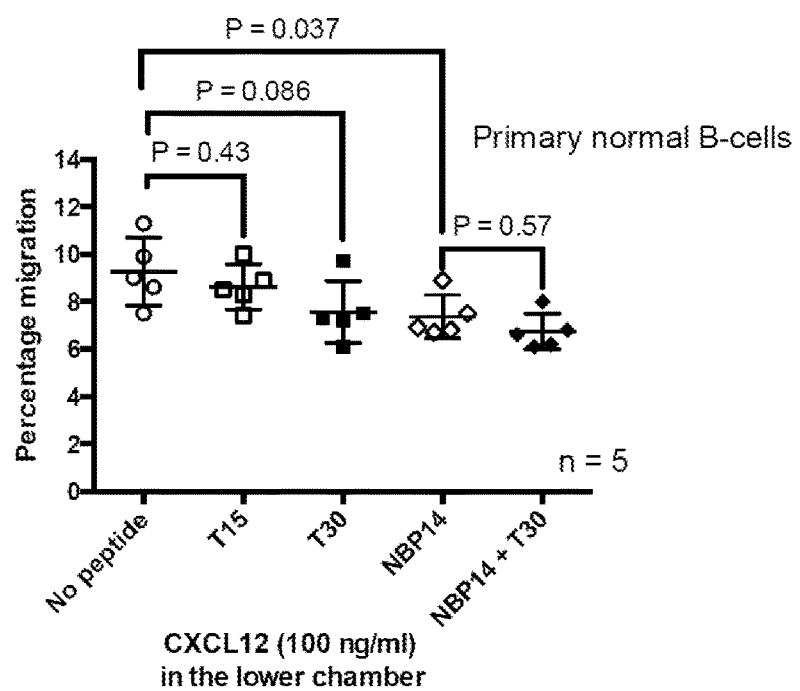
Figure 15:
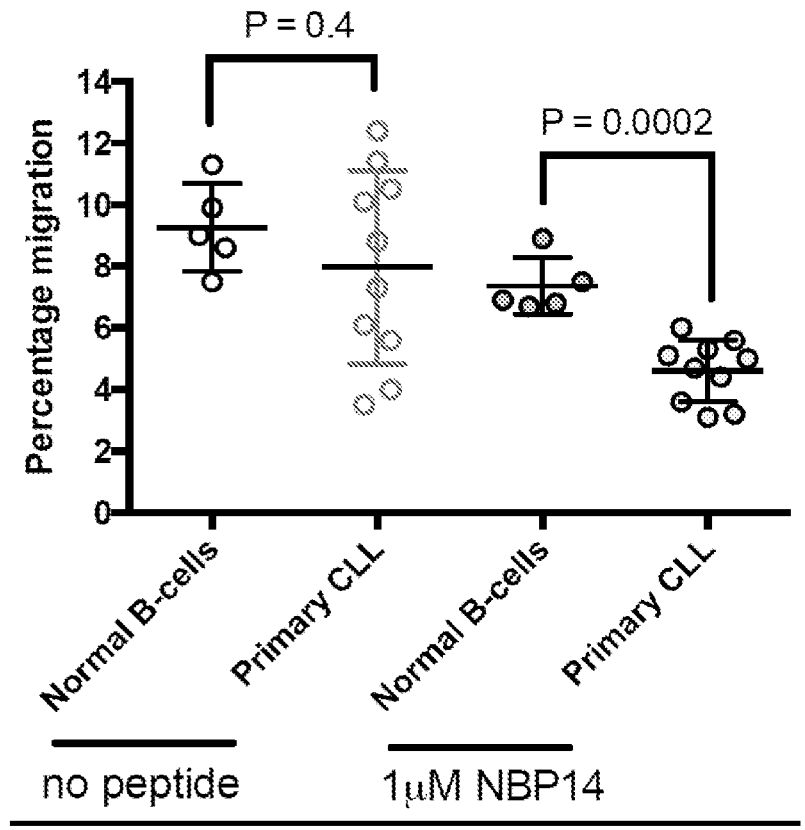
Figure 16:
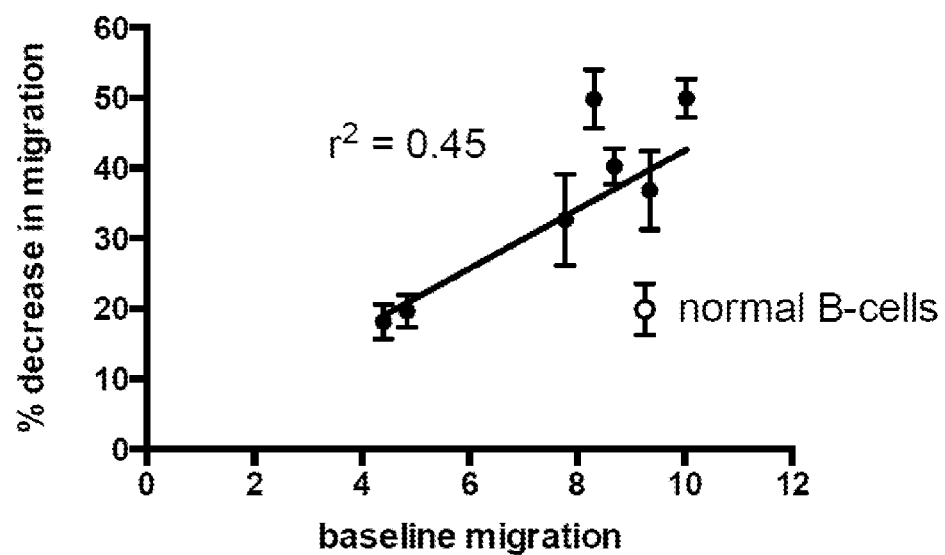
Figure 17:
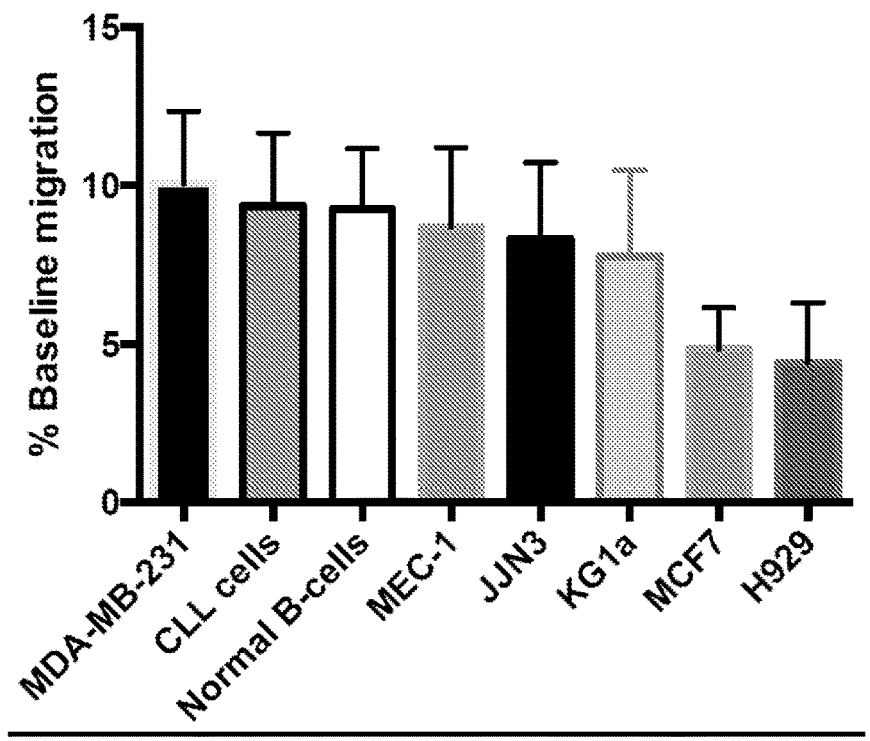
Figure 18:
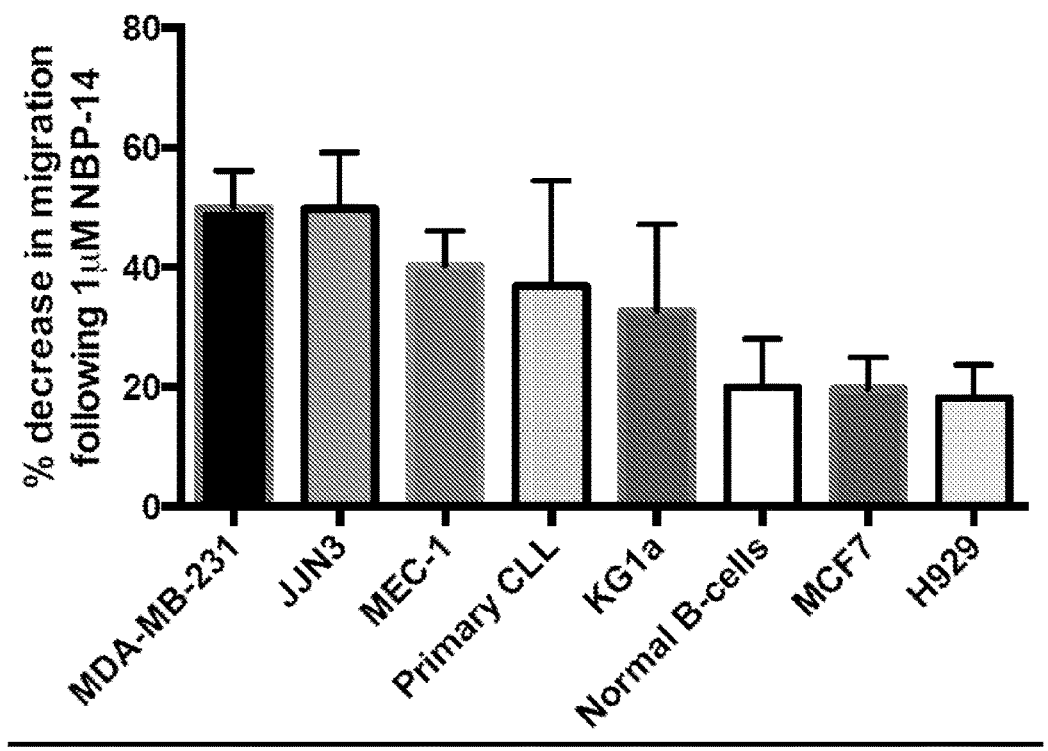

FIG. 4A shows a comparison of the cytotoxic effects of T15, T30, NBP-14 in primary CLL cells. FIG. 4(B) shows the effect of the anti-CD20 monoclonal antibody, Rituximab, is shown for comparison. All assays were carried out in duplicate and are presented as mean (±SD) of five independent experiments;

FIG. 5 shows a comparison of the effects of T15, T30, and NBP-14 peptides in normal B- and T-lymphocytes. All assays were carried out in duplicate and data are presented as mean (±SD) of three independent experiments;

FIG. 6 shows a comparison of the anti-proliferative effects of T15, T30 and NBP-14 in (A) MDA-MB-231 cells and (B) MCF7 cells. All assays were carried out in duplicate and data are presented as mean (±SD) of three independent experiments;

FIG. 7 shows a comparison of the anti-proliferative effects of T15, T30 and NBP-14 in (A) KG1a cells and (B) MEC-1 cells and (C) H929 cells. All assays were carried out in duplicate and data are presented as mean (±SD) of three independent experiments;

FIG. 8A shows the sequence of NBP-14 with the terminal Alanine (A) and Lysine (K) residues forming the cyclisation sites. FIG. 8B shows the cyclic NBP-14 peptide in which the terminal Alanine and Lysine residues are linked together;

FIG. 9 shows the comparison of the anti-migratory dose-responses induced by NBP-14 peptide in MDA-MB-231, MCF7, JJN3 and KG1a cancer cell lines. All data are presented as mean (±SD) of three independent experiments. *; $P<0.05$;

FIG. 10 shows the comparison of the anti-migratory effects of T15, T30, NBP-14 in the breast cancer cell lines (A) MCF7 and (B) MDA-MB-231. All data are presented as mean (±SD) of five independent experiments;

FIG. 11 shows the comparison of the anti-migratory effects of T15, T30, NBP-14 in the KG1a cell line. All data are presented as mean (±SD) of five independent experiments;

FIG. 12 shows the comparison of the anti-migratory effects of T15, T30, NBP-14 in the JJN3 cell line. All data are presented as mean (±SD) of five independent experiments;

FIG. 13 shows the comparison of the cytotoxic effects of T15, T30, NBP-14 in primary CLL cells. All assays were carried out in duplicate and data are presented as mean (±SD) of ten independent experiments;

FIG. 14 shows the comparison of the anti-migratory effects of T15, T30 and NBP-14 peptides on normal B-cells. All assays were carried out in duplicate and data are presented as mean (±SD) of five independent experiments;

FIG. 15 shows the comparison of the effects of NBP-14 peptides in primary CLL cells and normal B-lymphocytes. All assays were carried out in duplicate and data are presented as mean (±SD) of three independent experiments;

FIG. 16 shows the correlation between baseline migration and the percentage decrease in migration induced by NBP-14;

FIG. 17 shows the amount of baseline migration in a variety of cell lines in the absence of NBP-14, including MDA-MB-231, CLL cells, Normal B-cells, MEC-1, JJN3, KG1a, MCF7 and H929 cells; and FIG. 18 shows the percentage decrease in migration induced by 1 µM NBP-14 in a variety of cell lines, including MDA-MB-231, CLL cells, Normal B-cells, MEC-1, JJN3, KG1a, MCF7 and H929 cells.

EXAMPLES

Rationale

The inventors have generated a number of linear and cyclic peptides based on the C-terminus of acetylcholinesterase known as T15, T30 and NBP-14 peptides and evaluated their effects in a number of cell lines and primary leukaemia cells derived from patients. It should be noted that SEQ ID No: 3 is referred to herein as "cyclated T14", "CT14" or "NBP-14", and is a cyclic peptide with an amino acid sequence derived from the C-terminus of Tailed acetylcholinesterase.

Objectives

1. To determine the cytotoxic and cytostatic profile of NBP-14 in a range of human in vitro cancer models; and
2. To evaluate the effects of NBP-14 in normal B- and T-lymphocytes.

Materials and Methods

Cyclisation of Peptides

Three techniques were used to achieve cyclization of linear peptides described herein, i.e. side-chain-to-side-chain, side-chain-to-backbone, and head-to-tail (C-terminus to N-terminus) cyclization. Head-to-tail cyclization has been investigated extensively, and can involve directed Cys-Cys disulphide cyclization (up to two per molecule). Careful monitoring of the reaction ensures 100% cyclization. Two general approaches are used for synthesis: (1) classical solution-phase linear peptide cyclization under high dilution conditions; and (2) resin-based cyclization. Two distinct protocols were employed in the solid phase synthesis (1):

(a) The on-resin cyclization of a peptide anchored via a side-chain functional group, such as imidazole, 3 acid, 4 amine' or alcohol, was carried out. The peptide was orthogonally protected as an ester at the C-terminus, and the peptide was then assembled through regular Boc or Fmoc synthesis followed by saponification, cyclization and cleavage.

(b) Another protocol that was used was the cyclization cleavage approach, in which the cyclic peptide was synthesized by cyclization after step-wise linear peptide synthesis. One advantage of this method is that the side-chain does not need to be anchored, making the approach more general than (a). (Christopher J. White and Andrei K. Yudin (2011) Nature Chemistry 3; Valero et al (1999) *J Peptide Res.* 53, 76-67; Lihu Yang and Greg Morriello (1999) Tetrahedron Letters 40, 8197-8200; Parvesh Wadhwani et al (2006) J. Org. Chem. 71, 55-61).

KG1a, H929, MCF7, MDA-MB-231, MEC-1 and Primary CLL Cell Culture Conditions

The acute myeloid leukaemia (AML) KG1a cell line was maintained in RPMI medium (Invitrogen) supplemented with 100 units/ml penicillin, 100 µg/ml streptomycin and 20% foetal calf serum. The multiple myeloma (MM) cell line H929, the two breast cancer cell lines (MCF7 and MDA-MB-231), the MEC-1 cells and the primary chronic lymphocytic leukaemia cells were maintained in RPMI medium supplemented with 100 units/ml penicillin, 100 µg/ml streptomycin and 10% foetal calf serum. The media used contained acetylcholine but after the initial set of experiments an additional 100 µM of acetylcholine was added to the culture media. Cells were subsequently aliquoted ($10^6$ cells/ml) into 24-well plates and were incubated at 37° C. in a humidified 5% carbon dioxide atmosphere for 72 h in the presence of the peptides (T15, T30, NBP-14 and the combination of T30+NBP-14) at concentrations between 0.1 nM and 1 µM. In addition, control cultures were carried out to which no peptide was added. Cells were subsequently harvested by centrifugation and were analysed by flow cytometry using the Annexin V assay or were counted using a Vi-Cell XR cell viability counter (Beckman Coulter).

Measurement of in vitro Apoptosis

Cultured cells were harvested by centrifugation and then resuspended in 195 µl of calcium-rich buffer. Subsequently, 5 µl of Annexin V (eBiosciences) was added to the cell suspension and cells were incubated in the dark for 10 mins prior to washing. Cells were finally resuspended in 190 µl of calcium-rich buffer together with 10 µl of propidium iodide. Apoptosis was assessed by dual-colour immunofluorescent flow cytometry using an Accuri C6 flow cytometer and data were analysed using CFlow software (BD Biosciences).

Measurement of in vitro Proliferation

Cultured cells were harvested by centrifugation and were then counted using a Vi-Cell XR cell viability counter. The number of viable cells in each culture was then expressed as a percentage of the viable cells in the control cultures (no peptide).

Statistical Analysis

All statistical analysis was performed using Graphpad Prism 6.0 software (Graphpad Software Inc.).

In vitro Cytotoxicity Assay

The in vitro drug sensitivity was measured using the Annexin V/propidium iodide assay. Comparison of the effects of each peptide alone or in combination in the various cell lines and primary cells are shown below.

Example 1

Cyclic T14 (i.e. "NBP-14")

The 'tailed' acetylcholinesterase (T-AChE) is expressed at synapses and the inventors have previously identified two peptides that could be cleaved from its C-terminus, one referred to as "T14" (14 amino acids long), within the other which is known as "T30" (30 amino acids long), and which both have strong sequence homology to the comparable region of β-amyloid.

The amino acid sequence of the linear peptide, T14, is AEFHRWSSYMVHWK [SEQ ID No:3].

The amino acid sequence of the linear peptide, T30, is KAEFHRWSSYMVHWKNQFDHYSKQDRCSDL [SEQ ID No:2].

Another peptide referred to as "T15" corresponds to the last 15 amino acid residues of SEQ ID No:1, i.e. NQFDHYSKQDRCSDL [SEQ ID No: 4].

The AChE C-terminal peptide "T14"' has been identified as being the salient part of the AChE molecule responsible for its range of non-hydrolytic actions. The synthetic 14 amino acids peptide analogue (i.e. "T14"), and subsequently the larger, more stable, and more potent amino acid sequence in which it is embedded (i.e. "T30") display actions comparable to those reported for 'non-cholinergic' AChE.

Referring first to FIG. 8A, there is shown the 14 amino acid long cyclic T14 peptide (i.e. "NBP-14"). The cyclic peptide, NBP-14, has been cyclated via the terminal Alanine (A) and Lysine (K) residues, and is shown in FIG. 8B. Cyclisation can be achieved by several different means. For example, Genosphere Biotechnologies (France) performed the cyclisation of T14 by transforming the linear peptide into an N-terminal to C-terminal lactam. Cyclisation of T14 to create cyclic NBP-14 brings together both ends, i.e. HWK-AEF.

Example 2

Figure 1A:
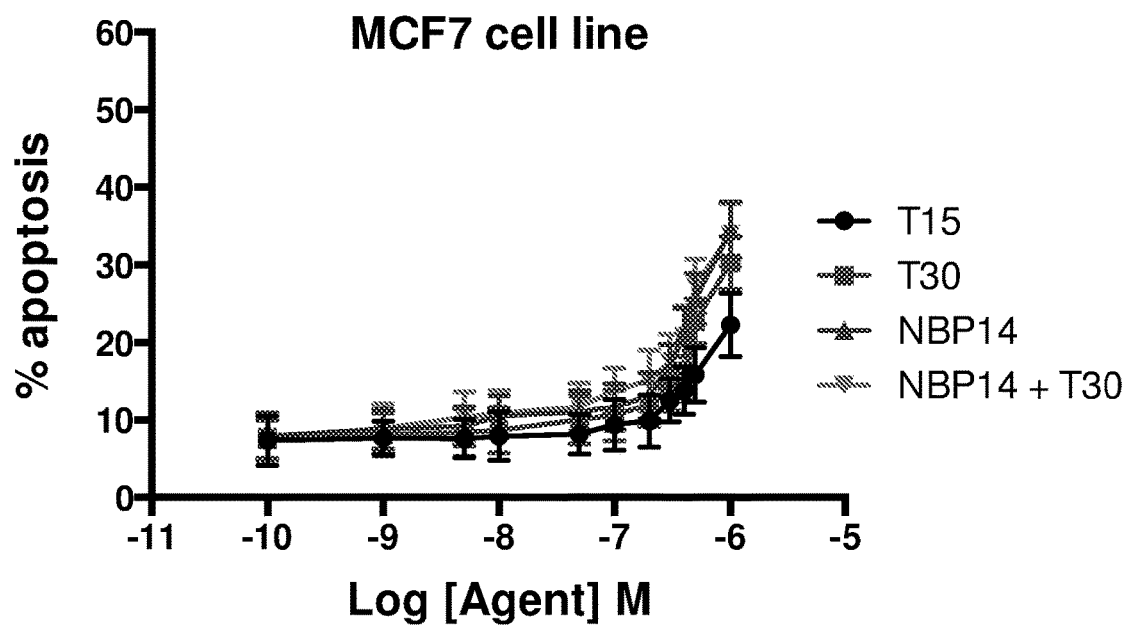
Figure 1B:
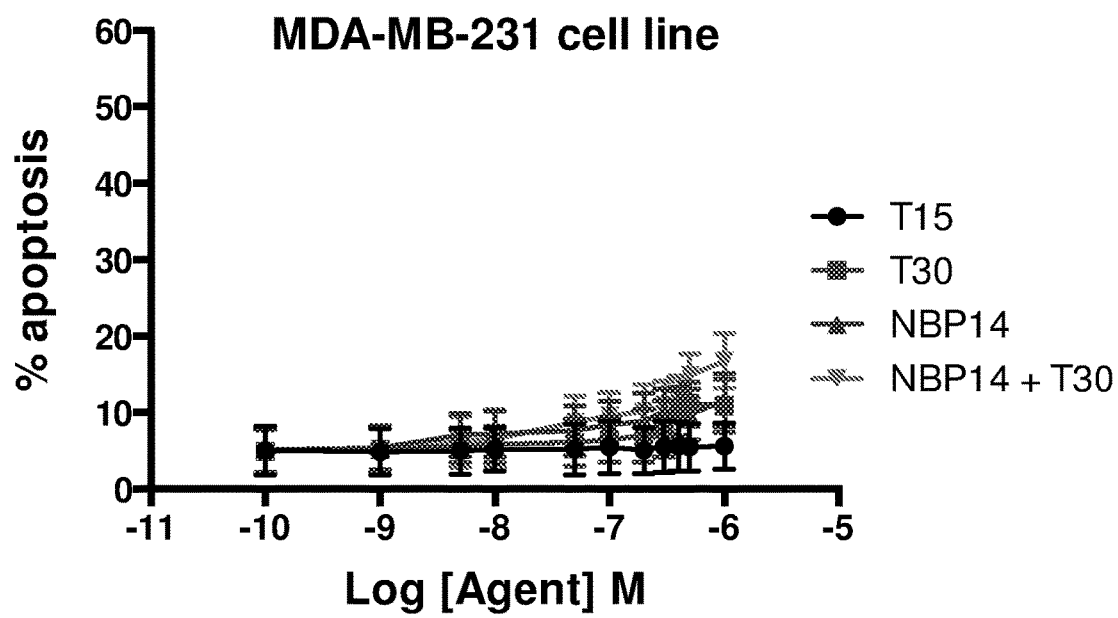

The effect of Acetylcholinesterase-Derived Peptides in the MCF7 and MDA-MB-231 Cell Lines The inventors examined the ability of the acetylcholinesterase-derived peptides (NBP-14 and/or T30) to induce apoptosis in the two breast cancer cell lines, and the results are shown in FIGS. 1A and 1B. The MCF7 cells showed evidence of apoptosis at peptide concentrations above 0.1 µM. The MDA-MB-231 cell line was less sensitive to the effects of the peptides under the same conditions.

Example 3

Figure 2:
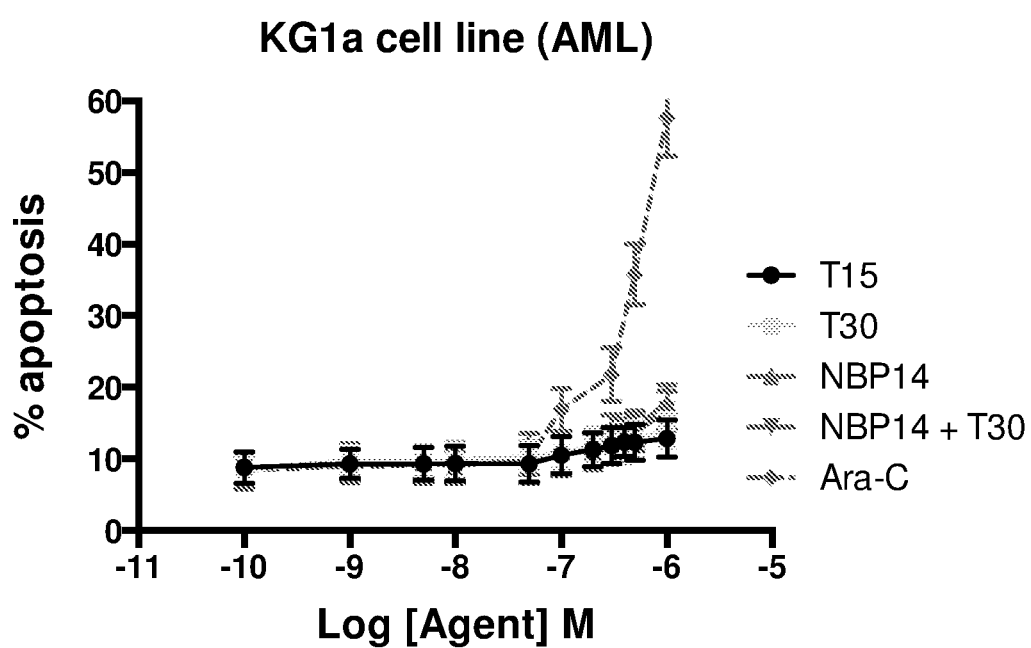
FIG. 2 shows a comparison of the cytotoxic effects of T15, T30, NBP-14 and Ara-C in the KG1a cell line. All assays were carried out in duplicate and are presented as mean (±SD) of three independent experiments.

The effect of the Acetylcholinesterase-Derived Peptides in the KG1a AML Cell Line KG1a cells were cultured with the peptides for 72 h and their apoptotic effects were assessed, and the results are shown in FIG. 2. For comparison, the KG1a cells were also cultured with Ara-C, a commonly used cytotoxic agent used for the treatment of AML. The acetylcholinesterase-derived peptides showed some toxicity in KG1a cells, and Ara-C showed a dose-response at concentrations above 0.1 µM.

Example 4

Figure 3A:
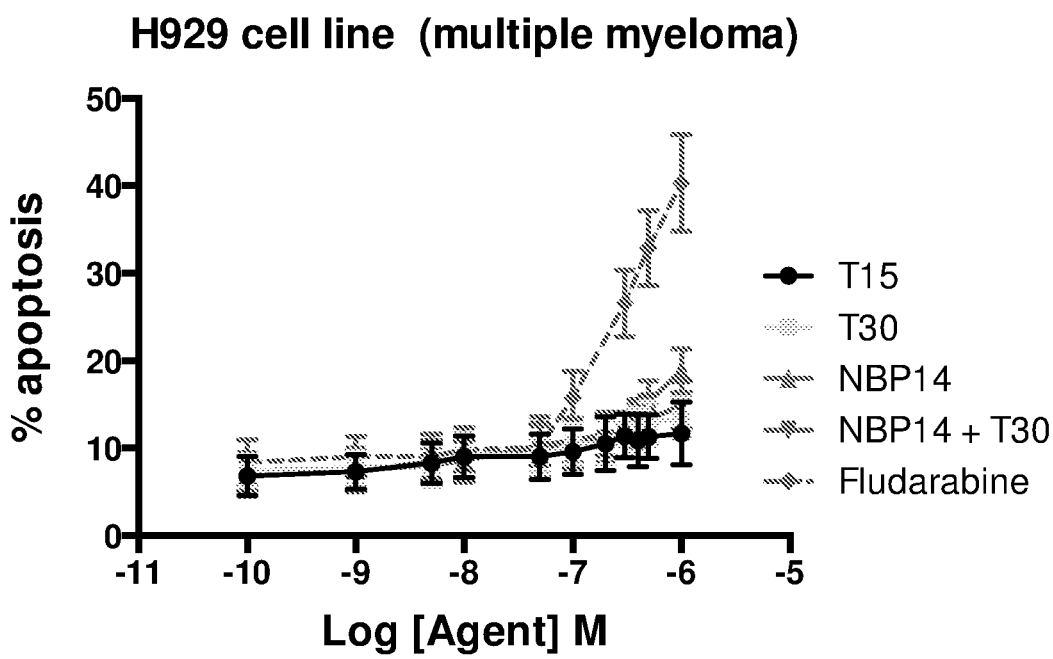
FIG. 3 shows a comparison of the cytotoxic effects of T15, T30, NBP-14 and fludarabine in (A) H929 and (B) MEC-1 cell lines. All assays were carried out in duplicate and are presented as mean (±SD) of three independent experiments.
Figure 3B:
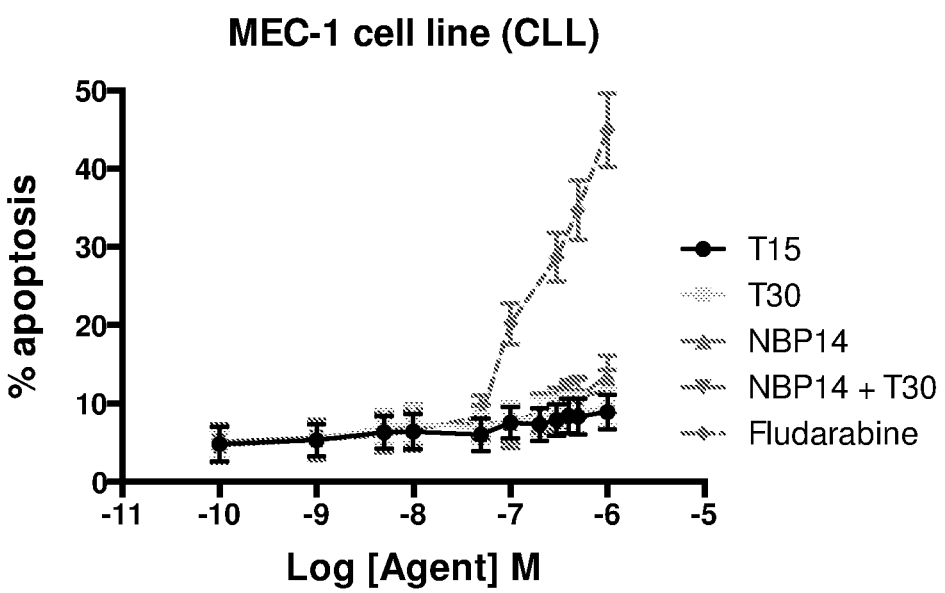

The Effect of the Acetylcholinesterase-Derived Peptides on H929 and MEC-1 B-Cell Lines The acetylcholinesterase-derived peptides showed a small cytotoxic effect in H929 cells and MEC-1 cells, and the results are shown in FIGS. 3A and 3B. The nucleoside analogue fludarabine induced a dose-response in both cell lines.

Example 5

The Effect of Acetylcholinesterase-Derived Peptides in Primary CLL Cells

The inventors next examined the effects of the acetylcholinesterase-derived peptides in primary CLL cells derived from patients, and the results are shown in FIGS. 4A and 4B. NBP-14 showed evidence of dose-response at concentrations above 0.1 µM. The effect on primary CLL cell viability was modest (~20% apoptosis at 1 µM). The inventors next compared this response with a non-genotoxic anti-CD20 monoclonal antibody (Rituximab). Rituximab induced a more pronounced dose-response at clinically used concentrations of the agent when compared to NBP-14.

Example 6

The Apoptotic Effect of Acetylcholinesterase-Derived Peptides in Normal B- and T-Lymphocytes In order to assess the effects of the acetylcholinesterase-derived peptides on normal (non-malignant) cells, B- and T-lymphocytes were isolated from normal healthy volunteers (n=3). The results are shown in FIG. 5. The peptides tested showed only modest toxicity in B- and T-lymphocytes.

Example 7

Figure 6A:
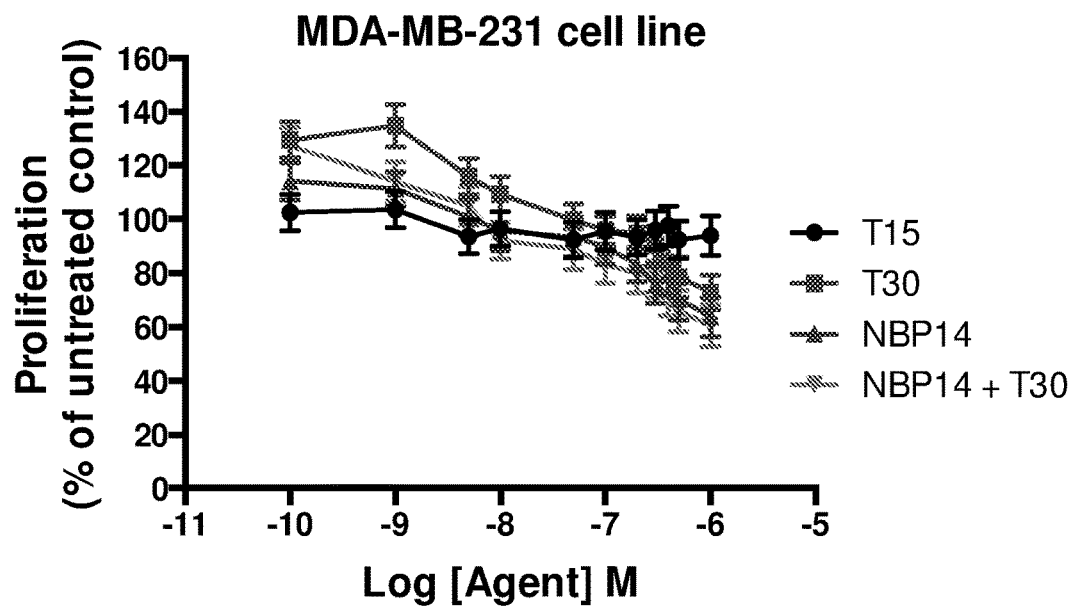
Figure 6B:
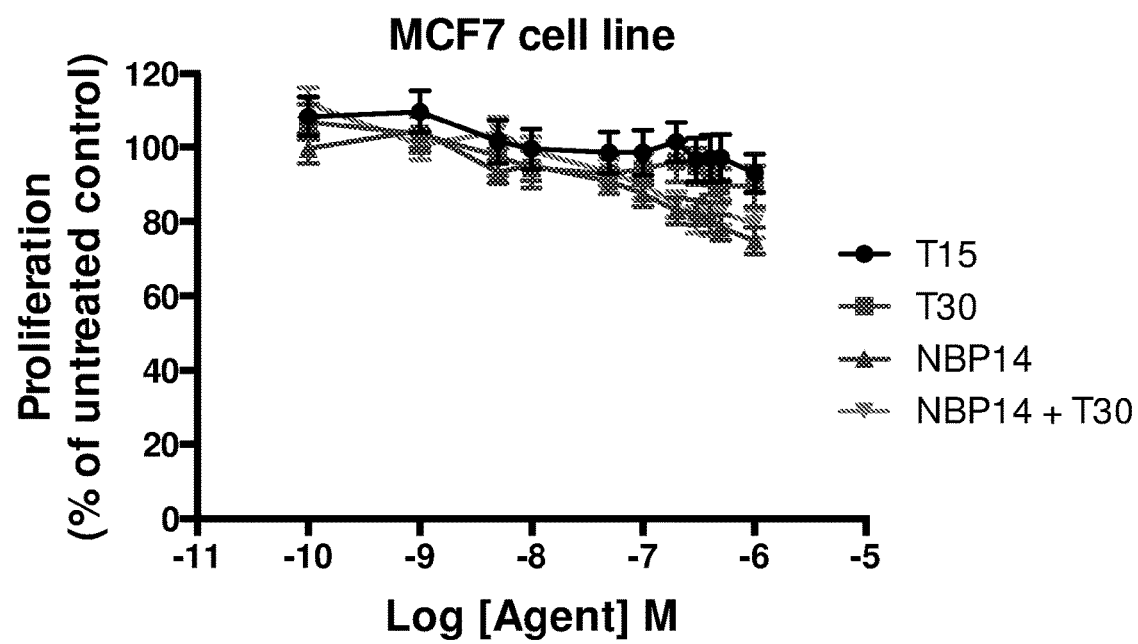

The Effect of the Acetylcholinesterase-Derived Peptides on Proliferation of the Cell Lines The inventors next examined the ability of the acetylcholinesterase-derived peptides to induce cytostasis, i.e. to inhibit proliferation in the various cell lines employed in this study. The results are shown in FIGS. 6A and 6B. The two breast cancer cell lines showed differential responses following incubation with the acetylcholinesterase-derived peptides. The more proliferative cell line MDA-MB-231 showed a significant reduction in proliferation with NBP-14 peptide concentrations above 0.1 μM when compared with the T15 control peptide. This effect was not as significant in the less proliferative MCF7 cell line. It is worthy of note that the MDA-MB-231 cell line showed increased proliferation in the presence of sub-nanomolar concentrations of T30 and NBP-14+T30.

Figure 7A:
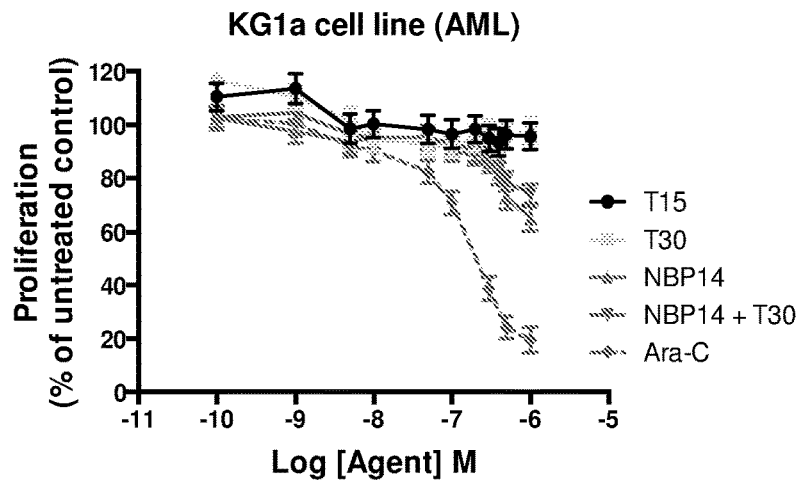
Figure 7B:
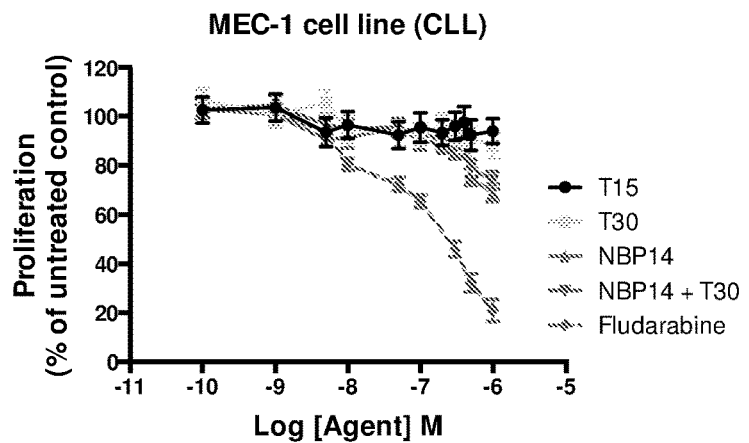
Figure 7C:
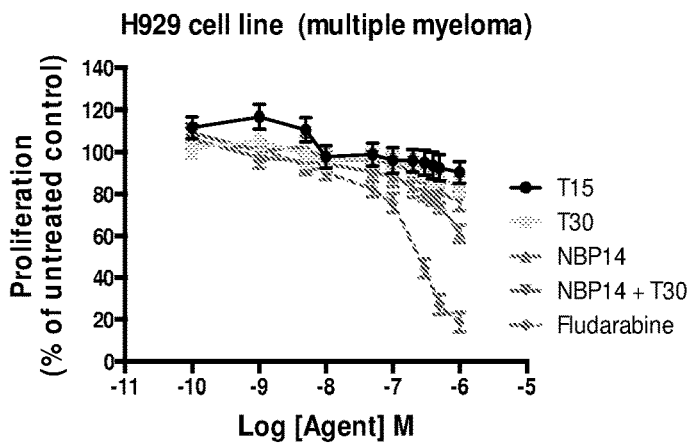

Referring to FIG. 7A-C, the KG1a cell line, the MEC-1 cell line and the H929 cell line all showed reduced proliferation following incubation with concentrations of NBP-14 above 0.1 μM. The effect of Ara-C (KG1a cells) and fludarabine (MEC-1 and H929 cells) are shown for comparison.

Conclusions
1. NBP-14 showed modest apoptotic effects in each of the cell lines tested at concentrations>0.1 μM. Although MCF7 cells showed relatively increased sensitivity to NBP-14, it was not preferentially cytotoxic in these cells when compared with the control peptide (T15) and the toxic peptide (T30).
2. None of the peptides tested appeared to show significant cytotoxic effects in normal B- and T-lymphocytes.
3. NBP-14 showed clear anti-proliferative activity in the migratory cell line, MDA-MB-231 cells. Similar effects were also observed in KG1a cells, MEC-1 cells and H929 cells with concentrations of peptide>0.1 μM. The anti-proliferative effects on MCF7 cells were less marked but this is the slowest growing of all the cell lines used in this study.
4. The lack of toxicity, in normal cells, of NBP-14 is encouraging.
5. Acetylcholinesterase-derived peptides including NBP-14 exhibit an anti-metastatic effect.

Based on the above findings, the inventors have demonstrated that cyclic peptides derived from the C-terminus of tailed acetylcholinesterase, and in particular, NBP-14, i.e. SEQ ID No.3, can be used to treat cancer and prevent metastasis. Accordingly, these cyclic peptides can be used as an adjuvant for the treatment of solid or metastatic tumours with chemotherapy/radiotherapy. This means that lower doses and exposure times of chemotherapy and/or radiotherapy are required.

Example 8

The Effects of NBP-14 on Migration in Cancer Cell Lines and Primary CLL Samples The following assays were performed in order to evaluate the potential anti-migratory (anti-metastatic) activity of NBP-14 shown in FIG. 8B:
1. Investigate the effects of NBP-14 on the in vitro migration of KG1a (Acute myeloid leukaemia cell line), JJN3 (Multiple myeloma cell line) and the breast cancer cell lines (MDA-MB-231 and MCF-7) using transwell assays.
2. Investigate the effects of NBP-14 on the in vitro migration of primary CLL samples using transwell assays.
3. Evaluate the effects of NBP-14 on the migration of normal B-cells.

MDA-MB-231, KG1a, and MEC-1 cells are highly migratory cancer cell lines. JJN3, CLL and MCF-7 are less migratory cancer cell lines. B-lymphocytes are normal, non-cancerous cells.

Rationale

The previous examples 1-7 indicated that an acetylcholinesterase-derived peptide inhibited endocytic activity in a human metastatic breast cancer cell line. The following examples were designed to establish whether the NBP-14 peptide had the potential to inhibit the migration of a number of cell lines and primary leukaemia cells derived from patients.

Objectives
1. To determine whether NBP-14 could inhibit tumour cell migration in a range of human in vitro cancer models.
2. To evaluate the effects of NBP-14 on the migration of normal B-lymphocytes.

Materials and Methods

KG1a, JJN3, MCF7, MDA-MB-231 and Primary CLL Cell and Normal B-Cell Culture Conditions The acute myeloid leukaemia (AML) KG1a cell line was maintained in RPMI medium (Invitrogen) supplemented with 100 units/ml penicillin, 100 μg/ml streptomycin and 5% foetal calf serum. The multiple myeloma (MM) cell line JJN3, the two breast cancer cell lines (MCF7 and MDA-MB-231), the primary chronic lymphocytic leukaemia cells and normal B-lymphocytes were maintained in RPMI medium supplemented with 100 units/ml penicillin, 100 μg/ml streptomycin and 5% foetal calf serum. In addition, 100 μM of acetylcholine was added to the culture media to ensure that the availability of acetylcholine was not a limiting factor in these experiments.

Migration Assays

In vitro migration assays were performed by using 6.0 μm pore size transwell migration plates (Costar, Corning, N.Y.). A total of $10^6$ CLL cells in 500 μl of RPMI media were added to the upper chamber of the transwell insert. 100 ng/ml of CXCL12 was added to the baso-lateral chamber for all the cell types tested apart from KG1a cells. These cells do not express CXCR4 and so are unresponsive to CXCL12. Instead, media containing 10% foetal calf serum was added to the baso-lateral chamber in these experiments. The plates were incubated for 24 h at 37° C. in 5% $CO_2$ in the presence of the peptides (T15, T30, NBP-14 and the combination of T30+NBP-14) at concentrations between 0.1 nM and 10 μM. In addition, control cultures were carried out to which no peptide was added. Cells were subsequently harvested by centrifugation and were analysed by flow cytometry using an Accuri C6 flow cytometer (BD). None of the conditions tested induced significant cell death in the cultures. Migration of CLL cells was determined by counting cells that migrated to the lower (baso-lateral) chamber of the transwell plate and then expressed as a percentage of the total number of cells initially added to the upper (apical) chamber.

Statistical Analysis

All statistical analysis was performed using Graphpad Prism 6.0 software (Graphpad Software Inc.).

Results

Initial experiments were performed to determine whether the acetylcholinesterase-derived peptide, NBP-14, altered the migration of a number of cancer cell lines in a dose-dependent manner. Referring to FIG. 9, the cell lines tested showed different baseline levels of migration (no peptide controls) but three of the four cell lines showed a significant decrease in migration when cultured with NBP-14 at concentrations≥1 μM. Only MCF7 cells failed to show a significant reduction in migration, but these cells showed the least migratory capacity under control (no peptide) conditions in any case.

Example 9

The Effect of Acetylcholinesterase-Derived Peptides in the MCF7 and MDA-MB-231 Cell Lines The inventors next examined the ability of 1 μM of the peptides to inhibit migration in the two breast cancer cell lines in 24 h transwell experiments. Referring to FIG. 10, MCF7 cells have only weak metastatic potential whereas MDA-MB-231 cells are highly metastatic. Accordingly, MCF7 cells showed less migration at 24 h when compared with MDA-MB-231 cells. NBP-14 had little effect on MCF7 cell migration (P=0.17). In contrast, the migration of MDA-MB-231 cells was significantly inhibited by NBP-14 (P<0.0001). Neither the T15 nor the T30 peptide showed a significant effect on the migration of MCF7 cells, whereas 1 μM T30 peptide significantly inhibited the migration of MDA-MB-231 cells (P=0.03). Furthermore, the T30 peptide was significantly less effective at inhibiting migration than NBP-14 (P=0.0013).

Example 10

The Effect of the Acetylcholinesterase-Derived Peptides in the KG1a Acute Myeloid Leukaemia Cell Line KG1a cells were cultured with the peptides for 24 h and their effects on migration were assessed. Referring to FIG. 11, NBP-14 (1 μM) significantly inhibited the migration of KG1a cells when compared to untreated (no peptide) controls (P=0.0017). In contrast, culture of KG1a cells with T15 and T30 peptides did not alter their migratory capacity (P=0.30 and P=0.14 respectively).

Example 11

The Effect of the Acetylcholinesterase-Derived Peptides on the JJN3 Multiple Myeloma Cell Line Referring to FIG. 12, in concordance with the MDA-MB-231 cell line data, the T15 peptide showed no significant effect on migration (P=0.43), whereas T30 and NBP-14 significant inhibited the migration of JJN3 cells (P=0.05 and P=0.0001 respectively). NBP-14 inhibited migration to a significantly greater extent when compared with T30 (P=0.0003) and the combination of NBP-14 and T30 peptide (both at 1 μM) did not significantly alter JJN3 cell migration when compared with NBP-14 alone under the conditions tested (P=0.15).

Example 12

The Effect of Acetylcholinesterase-Derived Peptides in Primary CLL Cells

The inventors next examined the effects of the peptides on the migratory activity of primary CLL cells derived from 10 patients. Referring to FIG. 13, there was considerable inter-patient variation in the migratory capacity of CLL cells tested (range 3.5%-12.4%) at 24 h. Treatment with 1 μM of T15 or T30 peptides did not significantly altered this (P=0.36 and P=0.11 respectively), whereas NBP-14 induced a significant reduction in migration (P=0.0046). The combination of T30+NBP-14 was no more effective at inhibiting CLL cell migration than NBP-14 alone (P=0.65).

Example 13

The Effect of Acetylcholinesterase-Derived Peptides in Normal B-Lymphocytes

In order to assess the effects of the peptides on normal (non-malignant) cells, B-lymphocytes were isolated from normal healthy volunteers (n=5). Referring to FIG. 14, NBP-14 induced a significant reduction in normal B-cell migration (P=0.037) whereas T15 and T30 peptides had no significant effect (P=0.43 and P=0.086 respectively). The combination of T30+NBP-14 did not significantly alter the migration of normal B-cells when compared with NBP-14 alone (P=0.57).

Example 14

Comparison of the Anti-Migratory Effects of NBP-14 in CLL Cells and Normal B-Cells Referring to FIG. 15, NBP-14 significantly inhibited the migratory activity of both primary CLL cells and normal B-cells. Analysis of the baseline migration of normal and malignant B-cells revealed no significant difference in the percentage of migrated cells at 24 h (P=0.4). Despite their similar inherent migratory potential, primary CLL cells were significantly more sensitive to the anti-migratory effects of NBP-14 when compared with normal B-cells (P=0.0002).

Example 15

Relationship Between Baseline Migration and Response to NBP-14

The inventors plotted the mean baseline percentage migration for each of the cell lines and primary cells tested against the percentage reduction in migration induced by 1 μM NBP-14. Referring to FIG. 16, there was clear relationship between the level of baseline migration and the anti-migratory response to NBP-14; high basal migration was associated with a larger percentage decrease in migration.

The relationship was even stronger when the normal B-cells were removed from the analysis.

Example 16

Comparison of Baseline Migration Between Various Cell Types and Prior to Exposure to NBP-14

The inventors investigated the percentage baseline migration (i.e. control) for the various cell lines under examination, and the results are shown in FIG. 17.

Then, these control values were compared in each cell line following exposure to 1 µM NBP-14, and the results are shown in FIG. 18. As can be seen, for all cell types, there is a significant reduction in cell migration. In other words, there is a clear reduction in metastasis in all cell lines.

Conclusions

1. NBP-14 showed significant anti-migratory effects in all of the cell lines tested with the exception of MCF7 cells, which showed the lowest basal migration under control (no peptide) conditions; an observation that is in keeping with the known low metastatic potential of these cells. Dose-response analysis revealed that NBP-14 was effective at inhibiting migration at concentrations≥1 µM. Therefore, all subsequent comparisons with control peptide (T15) and the toxic peptide (T30) were made at 1 µM.
2. None of the peptides induced significant cytotoxic effects in the cell lines or the primary malignant and non-malignant B-cells under the conditions tested. Therefore, the reductions in migration observed were not caused by increased cell death in the cultures.
3. The combination of the toxic peptide (T30) with NBP-14 had no significant effect on migration when compared with NBP-14 alone in any of the cell lines and primary cells evaluated.
4. Primary CLL cells showed baseline heterogeneity in their migratory capacity. However, NBP-14 was able to significantly reduce migration in these primary tumour cells.
5. Primary CLL cells were more sensitive than normal B-cells to the anti-migratory effects of NBP-14. This suggests that NBP-14 has utility as an anti-cancer therapeutic, particularly in those tumours that are prone to metastasis.
6. There is a significant reduction in cell migration or metastasis in all cell lines that were tested.

The invention claimed is:

1. A method of treating or ameliorating cancer in a subject, the method comprising, administering to a subject in need of such treatment, a therapeutically effective amount of a cyclized polypeptide of SEQ ID No:3, wherein the cancer is leukemia or multiple myeloma.

2. The method according to claim 1, wherein the cancer is leukemia.

3. The method according to claim 1, wherein the cancer is multiple myeloma.

* * * * *

SEQUENCE LISTING

```
<160> NUMBER OF SEQ ID NOS: 4

<210> SEQ ID NO 1
<211> LENGTH: 614
<212> TYPE: PRT
<213> ORGANISM: Homo sapiens

<400> SEQUENCE: 1

Met Arg Pro Pro Gln Cys Leu Leu His Thr Pro Ser Leu Ala Ser Pro
1               5                   10                  15

Leu Leu Leu Leu Leu Leu Trp Leu Leu Gly Gly Gly Val Gly Ala Glu
                20                  25                  30

Gly Arg Glu Asp Ala Glu Leu Leu Val Thr Val Arg Gly Gly Arg Leu
            35                  40                  45

Arg Gly Ile Arg Leu Lys Thr Pro Gly Gly Pro Val Ser Ala Phe Leu
        50                  55                  60

Gly Ile Pro Phe Ala Glu Pro Pro Met Gly Pro Arg Arg Phe Leu Pro
65                  70                  75                  80

Pro Glu Pro Lys Gln Pro Trp Ser Gly Val Val Asp Ala Thr Thr Phe
                85                  90                  95

Gln Ser Val Cys Tyr Gln Tyr Val Asp Thr Leu Tyr Pro Gly Phe Glu
                100                 105                 110

Gly Thr Glu Met Trp Asn Pro Asn Arg Glu Leu Ser Glu Asp Cys Leu
            115                 120                 125

Tyr Leu Asn Val Trp Thr Pro Tyr Pro Arg Pro Thr Ser Pro Thr Pro
        130                 135                 140

Val Leu Val Trp Ile Tyr Gly Gly Gly Phe Tyr Ser Gly Ala Ser Ser
145                 150                 155                 160

Leu Asp Val Tyr Asp Gly Arg Phe Leu Val Gln Ala Glu Arg Thr Val
                165                 170                 175

Leu Val Ser Met Asn Tyr Arg Val Gly Ala Phe Gly Phe Leu Ala Leu
                180                 185                 190

Pro Gly Ser Arg Glu Ala Pro Gly Asn Val Gly Leu Leu Asp Gln Arg
            195                 200                 205
```

```
Leu Ala Leu Gln Trp Val Gln Glu Asn Val Ala Ala Phe Gly Gly Asp
    210                 215                 220
Pro Thr Ser Val Thr Leu Phe Gly Glu Ser Ala Gly Ala Ala Ser Val
225                 230                 235                 240
Gly Met His Leu Leu Ser Pro Pro Ser Arg Gly Leu Phe His Arg Ala
                245                 250                 255
Val Leu Gln Ser Gly Ala Pro Asn Gly Pro Trp Ala Thr Val Gly Met
            260                 265                 270
Gly Glu Ala Arg Arg Arg Ala Thr Gln Leu Ala His Leu Val Gly Cys
        275                 280                 285
Pro Pro Gly Gly Thr Gly Gly Asn Asp Thr Glu Leu Val Ala Cys Leu
    290                 295                 300
Arg Thr Arg Pro Ala Gln Val Leu Val Asn His Glu Trp His Val Leu
305                 310                 315                 320
Pro Gln Glu Ser Val Phe Arg Phe Ser Phe Val Pro Val Val Asp Gly
                325                 330                 335
Asp Phe Leu Ser Asp Thr Pro Glu Ala Leu Ile Asn Ala Gly Asp Phe
            340                 345                 350
His Gly Leu Gln Val Leu Val Gly Val Val Lys Asp Glu Gly Ser Tyr
        355                 360                 365
Phe Leu Val Tyr Gly Ala Pro Gly Phe Ser Lys Asp Asn Glu Ser Leu
    370                 375                 380
Ile Ser Arg Ala Glu Phe Leu Ala Gly Val Arg Val Gly Val Pro Gln
385                 390                 395                 400
Val Ser Asp Leu Ala Ala Glu Ala Val Val Leu His Tyr Thr Asp Trp
                405                 410                 415
Leu His Pro Glu Asp Pro Ala Arg Leu Arg Glu Ala Leu Ser Asp Val
            420                 425                 430
Val Gly Asp His Asn Val Val Cys Pro Val Ala Gln Leu Ala Gly Arg
        435                 440                 445
Leu Ala Ala Gln Gly Ala Arg Val Tyr Ala Tyr Val Phe Glu His Arg
    450                 455                 460
Ala Ser Thr Leu Ser Trp Pro Leu Trp Met Gly Val Pro His Gly Tyr
465                 470                 475                 480
Glu Ile Glu Phe Ile Phe Gly Ile Pro Leu Asp Pro Ser Arg Asn Tyr
                485                 490                 495
Thr Ala Glu Glu Lys Ile Phe Ala Gln Arg Leu Met Arg Tyr Trp Ala
            500                 505                 510
Asn Phe Ala Arg Thr Gly Asp Pro Asn Glu Pro Arg Asp Pro Lys Ala
        515                 520                 525
Pro Gln Trp Pro Pro Tyr Thr Ala Gly Ala Gln Gln Tyr Val Ser Leu
    530                 535                 540
Asp Leu Arg Pro Leu Glu Val Arg Arg Gly Leu Arg Ala Gln Ala Cys
545                 550                 555                 560
Ala Phe Trp Asn Arg Phe Leu Pro Lys Leu Leu Ser Ala Thr Asp Thr
                565                 570                 575
Leu Asp Glu Ala Glu Arg Gln Trp Lys Ala Glu Phe His Arg Trp Ser
            580                 585                 590
Ser Tyr Met Val His Trp Lys Asn Gln Phe Asp His Tyr Ser Lys Gln
        595                 600                 605
Asp Arg Cys Ser Asp Leu
    610
```

```
<210> SEQ ID NO 2
<211> LENGTH: 30
<212> TYPE: PRT
<213> ORGANISM: Homo sapiens

<400> SEQUENCE: 2

Lys Ala Glu Phe His Arg Trp Ser Ser Tyr Met Val His Trp Lys Asn
1               5                   10                  15

Gln Phe Asp His Tyr Ser Lys Gln Asp Arg Cys Ser Asp Leu
            20                  25                  30

<210> SEQ ID NO 3
<211> LENGTH: 14
<212> TYPE: PRT
<213> ORGANISM: Artificial Sequence
<220> FEATURE:
<223> OTHER INFORMATION: NBP-14, a peptide derived from the C-terminus
      of acetylcholinesterase with terminal Alanine (A) and Lysine (K)
      residues required for cyclisation

<400> SEQUENCE: 3

Ala Glu Phe His Arg Trp Ser Ser Tyr Met Val His Trp Lys
1               5                   10

<210> SEQ ID NO 4
<211> LENGTH: 15
<212> TYPE: PRT
<213> ORGANISM: Homo sapiens

<400> SEQUENCE: 4

Asn Gln Phe Asp His Tyr Ser Lys Gln Asp Arg Cys Ser Asp Leu
1               5                   10                  15
```